United States Patent [19]

Batchelder et al.

[11] Patent Number: 5,133,602
[45] Date of Patent: Jul. 28, 1992

[54] PARTICLE PATH DETERMINATION SYSTEM

[75] Inventors: John S. Batchelder, Somers; Donald M. DeCain, New York; Philip C. D. Hobbs, Briarcliff Manor; Marc A. Taubenblatt, Pleasantville, all of N.Y.

[73] Assignee: International Business Machines Corporation, Armonk, N.Y.

[21] Appl. No.: 682,752

[22] Filed: Apr. 8, 1991

[51] Int. Cl.$^5$ .............................................. G01B 11/00
[52] U.S. Cl. .................................... 356/375; 356/364
[58] Field of Search .................. 356/375, 72, 73, 335, 356/336, 337, 338, 341, 343, 364; 377/11; 250/222.2

[56] References Cited

U.S. PATENT DOCUMENTS

| | | | |
|---|---|---|---|
| 2,679,183 | 5/1954 | Buchele et al. | 88/14 |
| 3,612,688 | 10/1971 | Liskowitz | 356/102 |
| 3,653,767 | 4/1972 | Liskowitz | 356/102 |
| 3,662,176 | 5/1972 | Kamentsky et al. | 250/218 |
| 3,676,647 | 7/1972 | Staffin et al. | 377/11 |
| 3,732,014 | 5/1973 | Uzgiris | 356/102 |
| 3,796,495 | 3/1974 | Laub | 356/109 |
| 3,901,602 | 8/1975 | Gravatt, Jr. | 356/114 |
| 4,011,013 | 3/1977 | Barrett | 356/75 |
| 4,099,875 | 7/1978 | McMahon | 356/103 |
| 4,164,373 | 8/1979 | Schuss et al. | 356/316 |
| 4,251,733 | 2/1981 | Hirleman, Jr. | 250/356 |
| 4,264,206 | 4/1981 | Hattori | 356/343 |
| 4,306,809 | 12/1981 | Azzam | 356/368 |
| 4,329,054 | 5/1982 | Bachalo | 356/336 |
| 4,387,993 | 6/1983 | Adrian | 356/336 |
| 4,477,187 | 10/1984 | Pettit et al. | 356/335 |
| 4,490,042 | 12/1984 | Wyatt | 356/340 |
| 4,526,468 | 7/1985 | Steigmeier et al. | 356/338 |
| 4,537,507 | 8/1985 | Hess | 356/336 |
| 4,540,283 | 9/1985 | Bachalo | 356/336 |
| 4,548,500 | 10/1985 | Wyatt et al. | 356/336 |
| 4,565,449 | 1/1986 | Grego | 356/361 |
| 4,577,964 | 3/1986 | Hansen, Jr. | 356/39 |
| 4,611,916 | 9/1986 | Yoshizumi | 356/349 |
| 4,632,554 | 12/1986 | Pearce | 356/349 |
| 4,636,075 | 1/1987 | Knollenberg | 356/336 |
| 4,662,749 | 5/1987 | Hatton et al. | 356/336 |
| 4,679,939 | 7/1987 | Curry et al. | 356/336 |
| 4,735,504 | 4/1988 | Tycko | 356/336 |
| 4,762,414 | 8/1988 | Grego | 356/349 |
| 4,764,013 | 8/1988 | Johnston | 356/349 |
| 4,772,127 | 9/1988 | Chase et al. | 356/338 |
| 4,776,699 | 10/1988 | Yoshizumi | 356/349 |
| 4,788,443 | 11/1988 | Furuya | 250/574 |
| 4,796,995 | 1/1989 | Salzman et al. | 356/368 |
| 4,799,796 | 1/1989 | Musha | 356/336 |
| 4,825,094 | 4/1989 | Borden et al. | 356/573 |
| 4,854,705 | 8/1989 | Bachalo | 356/336 |
| 4,927,268 | 5/1990 | Carr et al. | 356/336 |
| 5,037,202 | 8/1991 | Batchelder et al. | 356/338 |

OTHER PUBLICATIONS

Batchelder, "Interferometric detection of forward scattered light from small particles," APL, vol. 55, Jul. 17, 1989, No. 3, pp. 215–217.

See et al., "Scanning differential optical profilometer for simultaneous measurement of amplitude and phase variation," APL, Lett. 53(1), Jul. 4, 1988.

Heinrich et al., "A Noninvasive Optical Probe for Detecting Electrical Signals in Silicon IC's", Review of Progress in Quantitative Non-Destructive Evaluation Plenum Press, 1988, pp. 1161–1166.

E. Dan Hirleman, "Laser technique for simultaneous particle-size and velocity measurements" Optical Society of America 1978, vol. 3, No. 1, pp. 19–21.

*Primary Examiner*—F. L. Evans
*Attorney, Agent, or Firm*—Perman & Green

[57] ABSTRACT

A bright-field, particle position determining optical system is disclosed that uses both phase shift and extinction signals to determine particle trajectories. In a first embodiment, a pair of orthogonally polarized beams are positioned along an axis that intersects a particle's flow path at an acute angle. An optical system recombines the beams after they exit the flow path, the combined beams manifesting an elliptical polarization if a particle intersects one of the beams. Bright field detectors detect polarization components of the combined beam, provide a phase shift signal between the beam's orthogonal components and provide corresponding signals to a processor. The processor determines a signal asymmetry from the phase shift signal that is indicative of a particle's position in the flow path. Another embodiment of the invention examines a signal resulting from the beam's phase shift and determines a correction factor that is dependent upon the distance of the particle from the focal plane of the beams. Another embodiment employs a dithering system for cyclically moving one or more optical beams across a particle to further enable its trajectory or position to be determined.

25 Claims, 6 Drawing Sheets

TIME →

PARTICLE PATH DETERMINATION SYSTEM

FIELD OF THE INVENTION

This invention relates to the detection of small particles, and more particularly, to a system for determining the position of a particle in a flow cell.

BACKGROUND OF THE INVENTION

Particle counters and other instruments for detecting particles that are small compared to the wavelength of light, are typically obliged to detect particles at the focus of an optical beam. This enables a resulting signal to be enhanced by focussing the optical beam to a very small intense region. In such systems, particles traverse the focus region sufficiently quickly, even at low flow rates, that particle transit times are short compared to the time constants of mechanical vibrations and other noise sources. Further, the detection volume can be isolated to a region of the particle-containing fluid that is far from the windows between the optical elements and the fluid.

If the optical beam is non-uniform throughout the sensing volume, it is inevitable that particles of the same size, travelling with the fluid in different parts of the sensing volume, will produce different signals. The simplest cure for that effect is to restrict the fluid flow through an orifice that is sufficiently small that the optical response to a particle is essentially constant throughout the entire volume. This is impractical in strongly focussed systems because an orifice that is small will inevitably clog; large pressure drops are associated with fluids passing through such small orifices; and orifice walls interfere with the optical path.

The prior art illustrates many instruments and methods for detecting particles by measurement of "scattered" light intensity from a particle or collection of particles. "Forward direction" scattered light is generally excluded from the such measurements due to the presence of the incident beam. Forward direction scattered light is also known as "bright field" light. When the bright field is excluded (e.g. by masking), a "dark field" scattered light pattern results. It is known, however, that the relationship between a forward direction scattered light field from a small particle and a focussed incident beam is such that the particle causes a phase shift and an attenuation of the incident beam. The attenuation is called the extinction effect.

In U.S. patent application Ser. No. 07/184,639, now U.S. Pat. No. 5,061,070, entitled "Particulate Inspection of Fluids Using Interferometric Light Measurements", by Batchelder et al., and assigned to the same assignee as this application, the phase shift experienced by the forward direction field of an incident beam is employed to differentiate between bubbles and particles in a fluid. Batchelder et al. show that a small dielectric particle in a focussed, monochromatic light beam, produces a scattered wave in phase quadrature with the far-field incident beam. The forward direction scattered light is detected using an interferometer which measures the phase shift of one beam relative to another. A similar teaching by Batchelder et al. appears in Applied Physics Letters, Vol. 55, No. 3, July 1989, pp. 215-217.

In U.S. patent application, Ser. No. 07/547,735, now U.S. Pat. No. 5,037,202, entitled "Measurement of Size and Refractive Index of Particles Using the Complex Forward-Scattered Electromagnetic Field", by Batchelder et al., and assigned to the same assignee as this application, the phase shift and extinction experienced by a pair of incident beams are employed to characterize particles in a fluid. The two beams are orthogonally polarized and changes in signals derived from those beams (that occur when a particle passes therethrough) enable the particle to be classified with respect to its refractive index, and thus identified.

In many particle measuring systems which solely employ dark field scattered light (as contrasted to the forward-direction field employed by the above two referenced patent applications), signals derived from small particles therein show a dependence on the particle's trajectory. If the trajectory of the particle moves from a beam's focal plane, the signal waveforms are modified These modifications create non-uniform waveform shapes which are difficult to analyze.

One way to compensate for such non-uniform waveforms is described by Hirleman in "Laser Technique for Simultaneous Particle-Size and Velocity Measurements", Optics Letters, Vol. 3, No. pp. 19-21, (1978) and in U.S. Pat. No. 4,251,733. Hirleman describes how detected light-scatter exhibits several peaks in time as a particle travels through a two beam optical system. The trajectory of the particle is deduced from the height of those two peaks (see FIG. 4 of the patent and FIG. 3 of the Optics Letters article).

A somewhat more complicated trajectory correction system is described by Knollenburg in U.S. Pat. No. 4,636,075. Knollenburg employs coaxial beams of orthogonal polarization and coincident focal planes but differing spot sizes. Knollenberg's sensor requires that the signal from the tightly focussed spot rise above a threshold before taking the signal from the larger spot to obtain particle size.

In U.S. Pat. No. 4,662,749 to Hatton et al., a fiber optic probe is employed to project a fringe image into a measurement zone and then sense the resulting light perturbations which occur when a particle traverses the zone. Those perturbations are employed to enable calculation of the velocity and/or size of the particles.

A number of patents illustrate the use of several light beams to determine particle trajectory and other parameters such as velocity; however, in general, they employ dark field methods which do not allow maximal use of the available light intensity In U.S. Pat. No. 4,387,993 to Adrian, a dark field method is described in which concentric, annular incident beams of different focal spot size are used to determine whether a particle's trajectory is in the center of the larger beam. In U.S. Pat. No. 4,537,507 to Hess, a dark field method is described in which crossed beams of different focal spot size form a detection region with varying intensity patterns. In U.S. Pat. No. 4,540,283 to Bachalo, a dark field system is described in which two incident beams are crossed to set up an interference pattern that creates a varying signal when a particle passes therethrough. U.S. Pat. No. 4,764,013 to Johnston describes a dark field method that determines the phase difference between two polarization components of scattered light.

U.S. Pat. No. 4,788,443 to Furuya describes a dark field system wherein a single beam is projected into a particle-containing fluid. The scattered light is converted into electrical signals that are counted to derive the diameter and/or concentration of the particles. U.S. Pat. No. 4,854,705 to Bachalo describes another dark field system wherein concentric beams of different focal spot size are used to determine a particle's trajectory, in conjunction with detection optics which are confocal, thereby limiting the detection volume further. Carr et al. in U.S. Pat. No. 4,927,268 also describe a dark field method in which focal spots of varying size are used to determine whether a particle passes through the center portion of a larger beam. Optical fibers are employed to reduce alignment problems.

Accordingly, it is an object of this invention to provide an optical system which employs a bright field detection system for both detecting particles and determining their trajectories.

It is another object of this invention to provide an optical system for detecting particles in a fluid, which system compensates for particle trajectories that are not in the focal plane of an optical beam.

It is a further object of this invention to provide an optical system for measurement of extinction arising from beam/particle interaction, wherein the particle's flow direction is both known and unknown.

It is yet another object of this invention to provide a system for measurement of extinction arising from beam/particle interaction wherein artifacts in the light path are negated.

SUMMARY OF THE INVENTION

A bright-field, particle position determining optical system is disclosed that uses phase shift and/or extinction signals to determine particle trajectories. In a first embodiment, a pair of orthogonally polarized beams are positioned along an axis that intersects a particle's flow path at an angle. An optical system recombines the beams after they exit the flow path, the combined beams manifesting an elliptical polarization if a particle intersects one of the beams. Bright field detectors detect polarization components of the combined beam, provide a phase shift signal between the beam's components and provide corresponding signals to a processor. The processor determines a signal asymmetry from the phase shift signal that is indicative of a particle's position in the flow path. Another embodiment of the invention examines a signal resulting from the beams, phase shift and determines a correction factor that is dependent upon the distance of the particle from the focal plane of the beams. Another embodiment employs a dithering system for cyclically moving one or more optical beams across a particle to further enable its trajectory or position to be determined.

DETAILED DESCRIPTION OF THE INVENTION

The optical systems described hereinbelow employ phase shift and/or extinction information that arises from the presence of a particle in a focussed, coherent beam. Those quantities correspond to the real and imaginary parts of the complex, forward-scattered field of the beam. A description of the theory that underlies the phase shift and extinction effects can be found in the above-noted copending U.S. patent application, Ser. No. 07/547,735 filed Jul. 2, 1990 of Batchelder et al., the disclosure of which is incorporated herein by reference.

Figure 1:
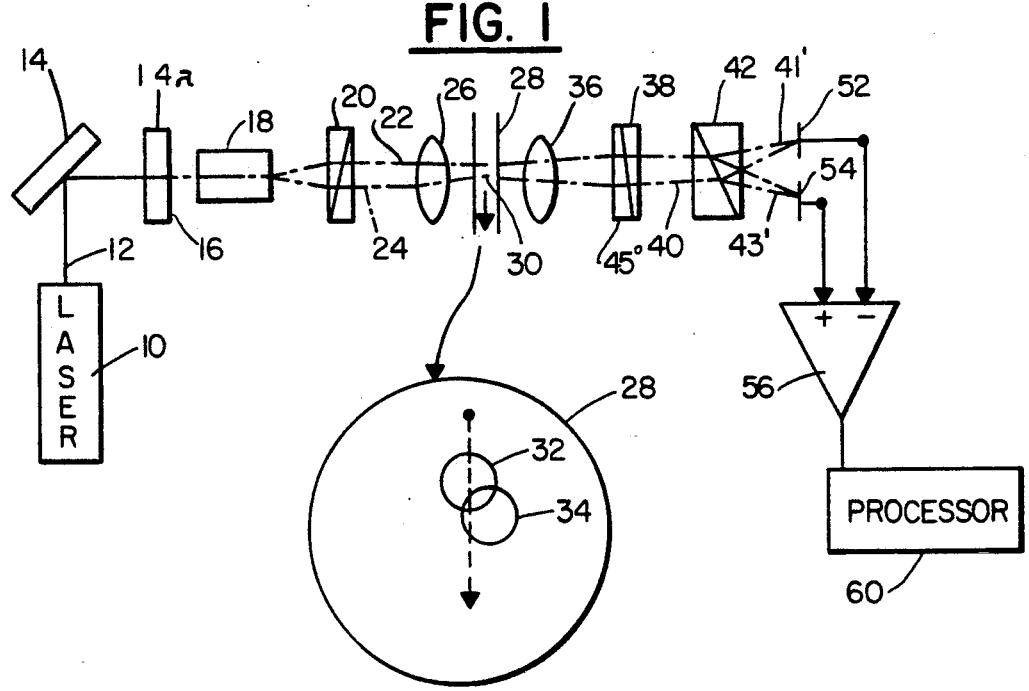
FIG. 1 is a schematic representation of an embodiment of the invention that enables determination of a particle's trajectory.

The embodiment of the invention shown in FIG. 1 is similar to that shown in the aforesaid Batchelder et al. application. It differs in certain respects, to wit: the arrangement of the optical beams with respect to each other and with respect to the particulate flow path, and the operation of the controlling microprocessor in response to signal inputs from the optical beams.

A laser 10 directs its beam 12 to a mirror 14, where it is reflected and passes through a quarter waveplate 16 to a beam expander 18. The expanded beam enters a Nomarski wedge 20 where orthogonal polarization components are caused to diverge into two substantially overlapping beams 22 and 24. Both beams are focussed by lens 26 into a flow cell 28, through which a particle 30 passes. Lens 26 causes two independent focussed spots to appear at the focal plane (substantially incident with the position of particle 30). Those spots are indicated as 32 and 34 in the expanded plan view of cell 28. A particle passing through a focussed beam will cause a phase shift and a change in its extinction, but will not affect the other beam until it enters thereinto.

Once the two beams exit from cell 28, they pass through a focussing lens 36 and enter a second Nomarski wedge 38, having the same orientation as first Nomarski wedge 20. There, the beams are recombined into a single expanded beam 40.

If no particle is present in cell 28, the combined vertical and horizontal polarization components of light beams 22 and 24 are equal, 90° out of phase, and the result is a circularly polarized beam 40 exiting from Nomarski wedge 38. If, by contrast, a particle 30 is present in the focal plane of one of the focussed beams within cell 28, that beam experiences a phase shift and creates an elliptical polarization of combined beam 40, as it exits second Nomarski wedge 38.

Combined light beam 40 is passed to a Wollaston prism 42 (oriented at 45° to Nomarskis 20 and 38) which separates the beam into its polarization components at an angle of 45° to the original Nomarski axes. Beam 41,, exhibits one axis of the elliptical polarization and is directed at photodetector 52, whereas orthogonally polarized beam 43' is directed at photodetector 54. Photodetectors 52 and 54 provide signals indicative of the intensities of incident beams 41' and 43', respectively, and their outputs are fed to a subtractive operational amplifier 56. A difference signal emanating from amplifier 56 is then fed to processor 60 for interpretation.

Figure 2:
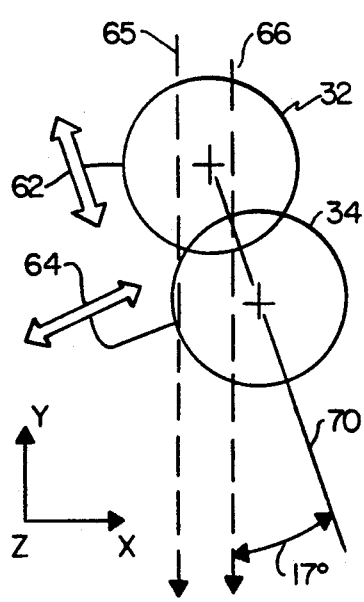
FIG. 2 is a detail showing the relationship of the optical beams that are employed to interrogate the particle flow path.

Referring to FIG. 2, the orientation of beams 32 and 34 and their relationship to particle flow paths will be considered in further detail. Beam 32 exhibits a polarization along axis 70 (as shown by arrows 62) and beam 34 a polarization perpendicular to axis 70 (as shown by arrows 64). A pair of particle flow paths are shown, one flow path 66 being close to the optical axis of beam 32 and the other flow path 68 offset to the left. It will be noted that beam 34 is offset from beam 32 by an angle that is measured between a line 70 connecting their optical axes and the directions of flow paths 66 and 68. That angle is termed the "twist" angle and defines the inspected volume within flow cell 28.

The twist angle determines how much of both beams a particle sees as it traverses both. What is important, therefore, is the distance along the x axis between the optic axes of beams 32 and 34. That distance is the beam waist times the sine of the twist angle. For beams separated by a beam waist, the system can operate with twist angles between about 5 to 45 degrees. It has been found preferable to set the twist angle between approximately 15° and 20° with an optimum setting being 17°. With a twist angle of 17 degrees, the x axis projection of the distance between the optic axes of beams 32 and 34, is sin 17° or 0.15 (beam diameter). At 5° the x axis projection is 0.04 times the beam diameter and at 45°, 0.35 times the beam diameter.

Assume first that a particle passes through beams 32 and 34 on flow path 66. As indicated above, dependent upon the distance of the particle from the beam's optical axis, a particle passing through a beam will induce a phase shift in the beam. It will further be recalled that a phase shift of one beam with respect to the other results in elliptical polarization of the combined beams. The elliptical polarization components are separated in Wollaston prism 42 and directed to a pair of photodetectors 52 and 54. Thus, as a particle passes through beam 32 on path 66, a phase shift is induced therein, which phase shift causes a change in the intensity of the elliptical polarization components 41' and 43'.

It is to be understood that each of detectors 52 and 54 develops bipolar signals as a particle passes therethrough. While a single detector sensing a prescribed polarization axis could be utilized to produce an appropriate bipolar phase shift signal, the use of two detectors enables differential amplifier 56 to remove common noise from these signals and to pass a single bipolar signal to processor 60.

As aforestated, each detector develops both a positive and a negative pulse as a particle passes sequentially through each beam. This is because the system fundamentally measures the phase shift induced by the particle. When the particle is in the first beam, it (typically) induces a phase lag in that beam with respect to the second. This shows up as a drop in signal from one detector and an increase from the other. When the particle is in the second beam, the phase lag that it induces in the second beam is indistinguishable from a phase lead in the first beam, and the signal increases in the first detector, while decreasing in the other. In more detail, assume that one beam is polarized vertically and the other horizontally, and that the phase of one beam is 90 degrees delayed with respect to the other. Circularly polarized light emerges from the sensing volume in the absence of particles; and has the characteristic that a linear polarizer can be placed in the beam at any orientation and transmits the same amount of power. Suppose the analyzing polarizer is at 45 degrees. If the phase lag between the two beams is increased to 180 degrees then the $+y$ component of the first beam is in phase with the $-x$ component of the second. The result is linearly polarized light oriented such that nothing gets through the analyzing polarizer, and a detector sees a big drop in signal strength. Similarly, if the phase lag is decreased to 0 degrees, the output is linearly polarized in the $+y$ x direction so that now all the light hits the detector; and it sees twice the signal of the circularly polarized nominal case.

In summary, until a particle is present in either of beams 32 or 34 the output of differential amplifier 56 is essentially nulled. When a particle enters beam 32 and passes therethrough, a phase shift is induced, causing a change in the beam's polarization axes. As a result, the output from amplifier 56 resembles waveform 72 in FIG. 3. When the particle continues on path 66 through beam 34, the resulting phase shift causes a change in the ellipticity of the polarization axes of beam 34, which change is sensed and the output of amplifier 56 is caused to resemble waveform 74 in FIG. 3. The closer that path 66 takes to a bisector (not shown) between the optical axes of beams 32 and 34, the more identical will be the shapes of waveforms 72 and 74.

By contrast, if a particle takes path 68 past beams 32 and 34, the resulting waveform from amplifier 56 will resemble curves 76 and 78 respectively. It can thus be seen that through analysis and comparison of succeeding waveforms from amplifier 56, that the distance of a particle's trajectory from beams 32 and 34 can be determined. Thus processor 60, after conversion of the waveforms into digital form, looks at the ratio of the signal peaks and, finds the off-axis distance of a particle.

As noted in copending U.S. patent application 07/547,735, the outputs of detector 52 and 54 (FIG. 1) can be summed to produce an extinction signal. To obtain an optimum extinction signal wherein noise is reduced, a portion of the beam from flow cell 30 can be diverted and passed through another Wollaston so that one beam corresponding to spot 32 falls on one detector and a beam corresponding to spot 34 falls on another. By then differentially sensing the resulting signals, a bipolar extinction signal can be derived in which the heights of the signal peaks can also be used to determine a particle trajectory.

The actual off-axis distance cannot be analytically calculated from the signal peak ratios. As a result, processor 60 is provided with a table of calculated ratios for known off-axis distances. The actual ratio measurements are compared therewith and interpolated so as to determine the actual distances. The manner of calculating the values in that table will be considered in the Derivation section below.

The choice of a 17° twist angle is not random. The greater the twist angle, the greater the accuracy with which a particle's trajectory can be computed. With very small twist angles, electrical noise tends to obscure the measured asymmetry so that it is difficult to correct for trajectory. Modelling the performance of the system to find, for a largest ratio of large to small waveform peaks of 3 to 2, a 17° twist angle typically provides a particle diameter measurement accuracy of approximately 10%. It also provides an optimum inspected volume that improves counting statistics of the sensor. As the twist angle is increased, the usable inspection volume decreases (a narrower strip of trajectories is accommodated).

Figure 3:
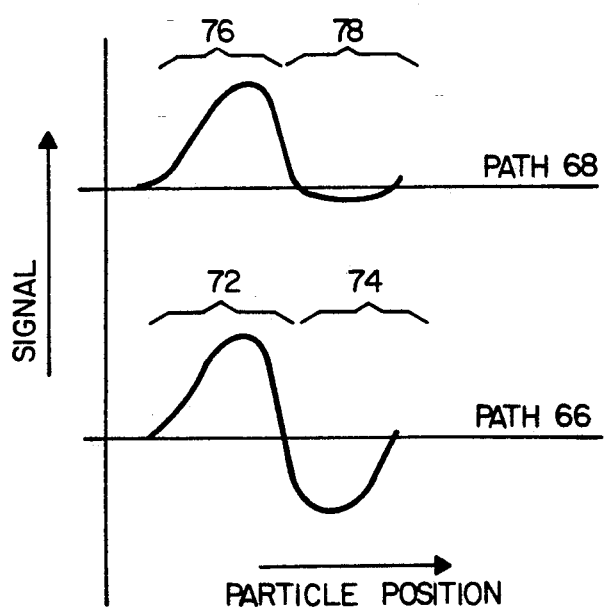
FIG. 3 shows two waveforms that result from two different particle trajectories in the system of FIG. 1.
Figure 4:
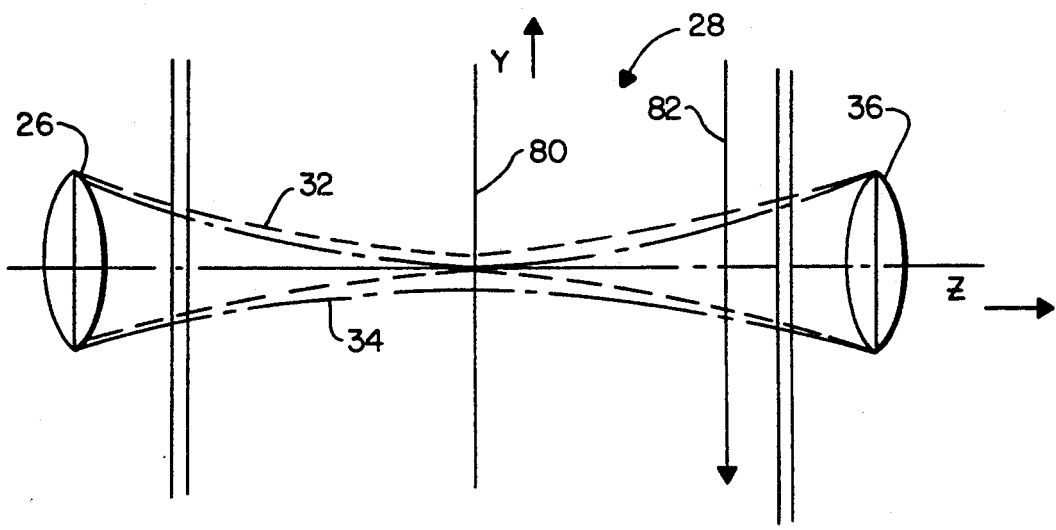
FIG. 4 is a side view of a particle flow path showing one particle passing through the focal plane of a pair of interrogating beams and another particle having a flow path removed from the focal plane.

Referring now to FIG. 4, the relationship of lenses 26 and 36 and beams 32 and 34 are represented as seen perpendicular to the Z axis of flow cell 28. Both beams 32 and 34 are focussed by lens 26 onto focal plane 80. Any particle having a flow path coincident with focal plane 80 will always generate constant width signals (as shown in FIG. 3) due to the predetermined beam sizes of beams 32 and 34 at focal plane 80. On the other hand, a particle passing at some constant out-of-focus distance from focal plane 80 (e.g., path 82), will result in a distortion in signal waveform widths emanating from amplifier 56.

Figure 5:
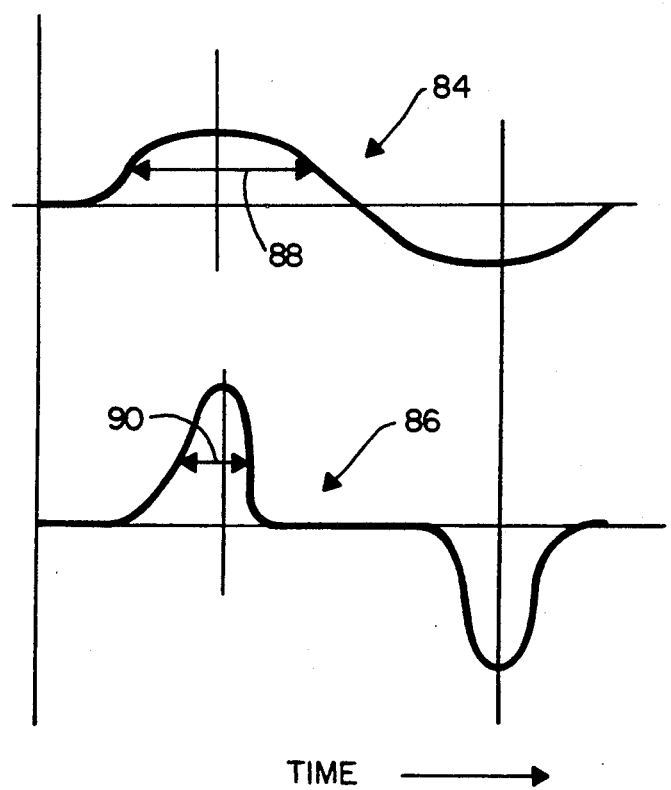
FIG. 5 indicates a pair of waveforms which result from the flow path trajectories shown in FIG. 4.

As shown in FIG. 5, a particle passing through beams 32 and 34 on path 82 (oriented with respect to beams 32 and 34 as indicated by path 66 in FIG. 2), will create a signal waveform as shown at 84 in FIG. 5. By contrast, a similarly oriented particle whose flow path coincides with focal plane 80 will result in a waveform as shown at 86. To determine the offset of a particle's trajectory from focal plane 80, the widths of waveforms 84 and 86 are compared to enable a correction factor to be derived.

Each waveform is characterized by a measurement taken of its width at ½ of its maximum value. This measurement is termed "full width at half maximum" or FWHM. The FWHM of waveform 84 is illustrated by line 88, whereas the FWHM of waveform 86 is illustrated by line 90. Within processor 60 (shown in FIG. 1), FWHM values for curve 86 (i.e. particle path is coincident with focal plane 80) will have been precalculated and stored. When the FWHM for curve 84 is calculated (after measurement), the ratio of FWHM 88 to FWHM 90 is calculated and a correction factor is derived therefrom. That correction factor is directly related to the out-of-focus distance of a particle path from the focal plane.

First the out of focus distance is determined by the pulse width method described with respect to FIGS. 4 and 5, then the distance of closest approach (off axis distance) is determined from the asymmetry calculations described with respect to FIGS. 2 and 3. The observed pulse heights can then be corrected for the particle trajectory thereby producing an accurate "binning" signal, namely the signal that would have been produced if the particle had a perfect trajectory in focus and on axis. The derivation and the use of the above-noted correction factors is shown in part 4 of the Derivation section of this application.

It should further be noted, as a particle's trajectory becomes further off axis or out of focus, the pulse heights which must be measured become smaller. A limit will be reached, due to background noise levels, for which the signals will be too small to accurately determine the trajectory. This limit will be reached sooner for small particles (i.e. which produce small signals) than for large particles Thus large particles can be detected further off axis or out of focus, than small particles, i.e. the inspection volume is dependent on particle size. To accurately determine the concentration of a given size particle, this inspection volume should be known. It will be recalled that the above-described corrections enable a signal to be derived as if the particle had had a perfect trajectory. However, the derived signal strength, assuming a perfect trajectory, is related to the particle's size (without the affects of off-axis trajectories). The inspection volume may be determined by using a table of allowed off-axis distances (asymmetries) and a table of allowed out-of-focus distances as a function of particle size (signal level). Thus, given a particle signal level, after correction, if the particle's off-axis or out-of-focus distances are greater than predetermined values stored in a table, then the particle signal is ignored due to likely corruption by background noise levels. The allowable distances are determined by the signal to noise levels for the various particle sizes.

Figure 6:
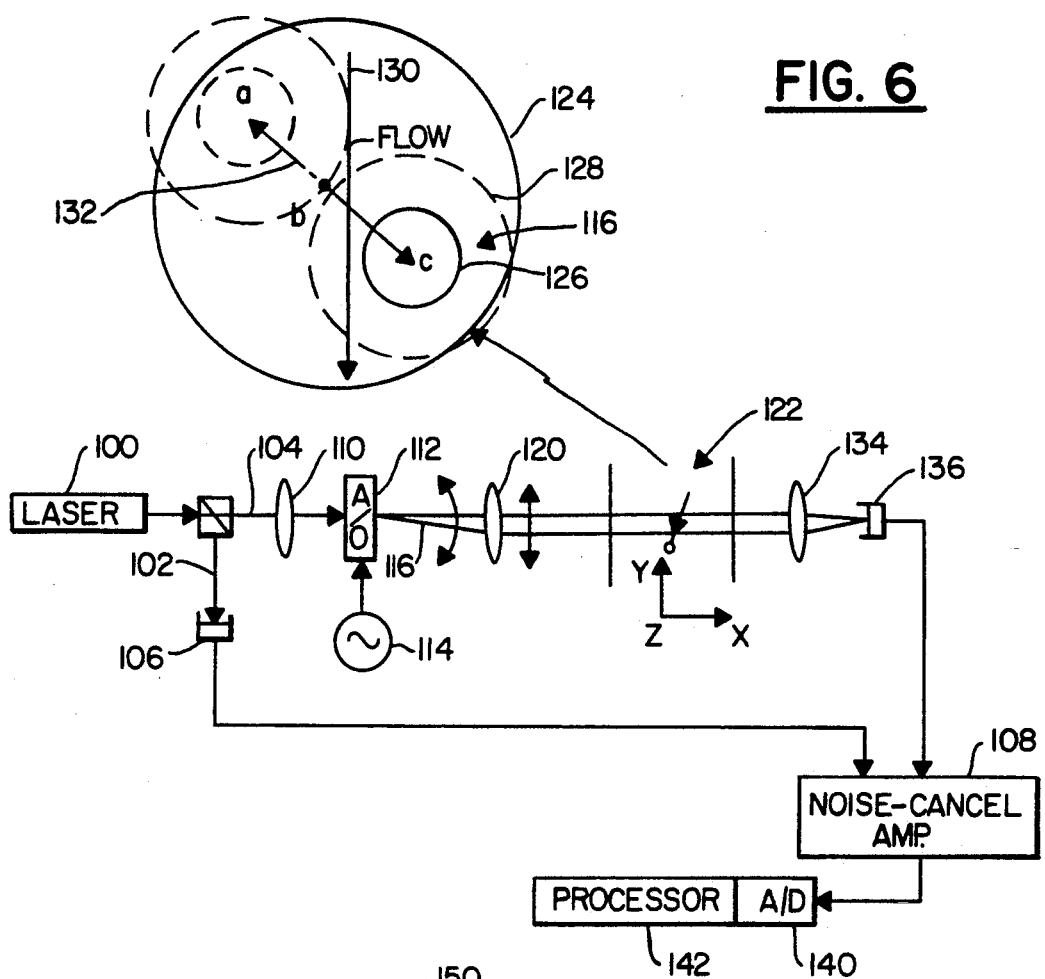
FIG. 6 is a schematic representation of another embodiment of the invention which employs a single dithered beam for particle trajectory determination.

The optical system of FIG. 1 employs a pair of fixed coherent beams to determine beam trajectory. In FIG. 6, it is shown how trajectory measurements can be obtained through the use of single optical beam. The system of FIG. 6 dithers a single beam very rapidly, with the dither period being much shorter than the time a particle spends in the beam. A particle traversing the dither path will thus produce an oscillating signal burst at the dither frequency, so band pass or phase lock methods are used to isolate the signal. By orienting the dither axis at an angle to the flow direction, a particle's trajectory may be similarly calculated as described with respect to FIG. 1.

A laser 100 (FIG. 6) produces a beam which is split to obtain a reference beam 102 and a primary beam 104. Reference beam 102 is detected by photodetector 106 and fed into a differential, noise cancelling amplifier 108. Primary beam 104 is focussed by lens 110 onto an acousto-optic deflector which produces a beam deflection according to a dither voltage source 114. Dithered beam 116 is collimated by lens 120 and passes through flow cell 122.

A view of flow cell 122, showing a plan view of the YZ plane therein, is shown at 124. Dithered beam 116 is, in actuality, a beam that exhibits a gaussian distribution of intensities. Thus, inner circle 126 illustrates the area of highest intensity, whereas outer circle 128 illustrates the extent of the gaussian intensity skirts. Beam 116 is dithered between positions a and c at a twist angle illustrated by the angle between flow path 130 and dither axis 132.

As above-stated, dithered beam 116 is dithered at a frequency that is large compared to the time a particle spends in the beam, and thus passes over the particle many times during the particles transit through flow cell 122. Thus, if a particle is positioned at point b in cell 122, it induces in beam 116 a change in the beam's extinction that varies as the dither frequency.

When beam 116 exits from inspection cell 122, it is focussed by lens 134 onto a photodetector 136. The signal from photodetector 136 is applied to noise cancelling amplifier 108 and is differenced therein with the reference signal provided by photodetector 106. The output of noise cancelling amplifier 108 is essentially nulled until a particle intercepts dithered beam 116 and produces a time varying extinction signal.

Figure 7:
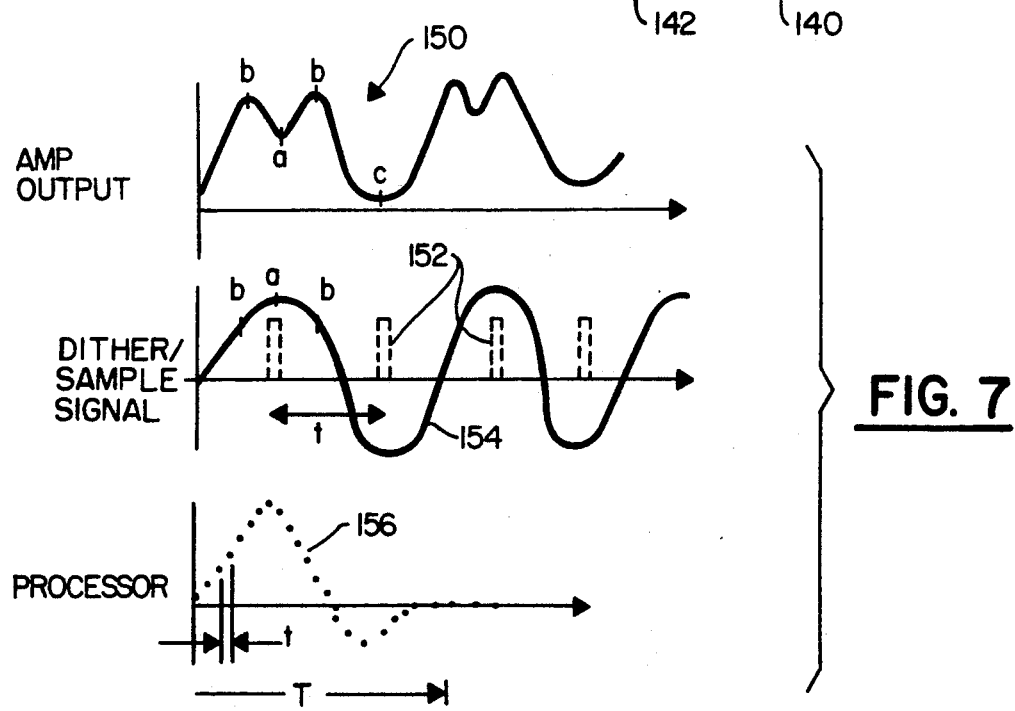
FIG. 7 shows waveforms useful in understanding the operation of the embodiment of FIG. 6.

The waveform output from amplifier 108 is shown by curve 150 in FIG. 7. The shape of curve 150 can be understood by realizing that the extinction of beam 116 is greatest when it is centered on the particle on point b, and results in a minima in the extinction signal from photodetector 136 at that point The resulting output from noise cancelling amplifier 108 (because it is a differential signal) is thus at a maximum when beam 116 is centered on a particle at point b. When beam 116 traverses to point a, the output from noise cancelling amplifier 108 does not revert to a null due to the fact that the particle still affects the extinction of beam 116 as a result of its presence in the skirt area 128 of the beam. When beam 116 returns to point c, the particle is not encompassed by skirt area 128 and the output from noise cancelling amplifier 108 reaches a null.

Waveform 150 is applied to analog to digital converter 140 whose output is, in turn, applied to processor 142. Within processor 142, a periodic signal 152 is generated to sample waveform 150 when the beam 116 reaches points a and c respectively. The relationship of sampling signals 115 to dither voltage 154 can be seen in the middle waveform diagram of FIG. 7. Thus, voltage samples are derived from waveform 150 at time intervals t. Processor 142 stores the sampled voltages and constructs a signal over a longer time interval T to obtain a waveform corresponding to that derived in FIG. 1 for a particle travelling through flow cell 22. Thus, reconstructed signal 156 is identical to the waveforms obtained with two static beams and identical methods can be used to determine a particle's off-axis position, out-of-focus position and signal and volume corrections derived.

Figure 8:
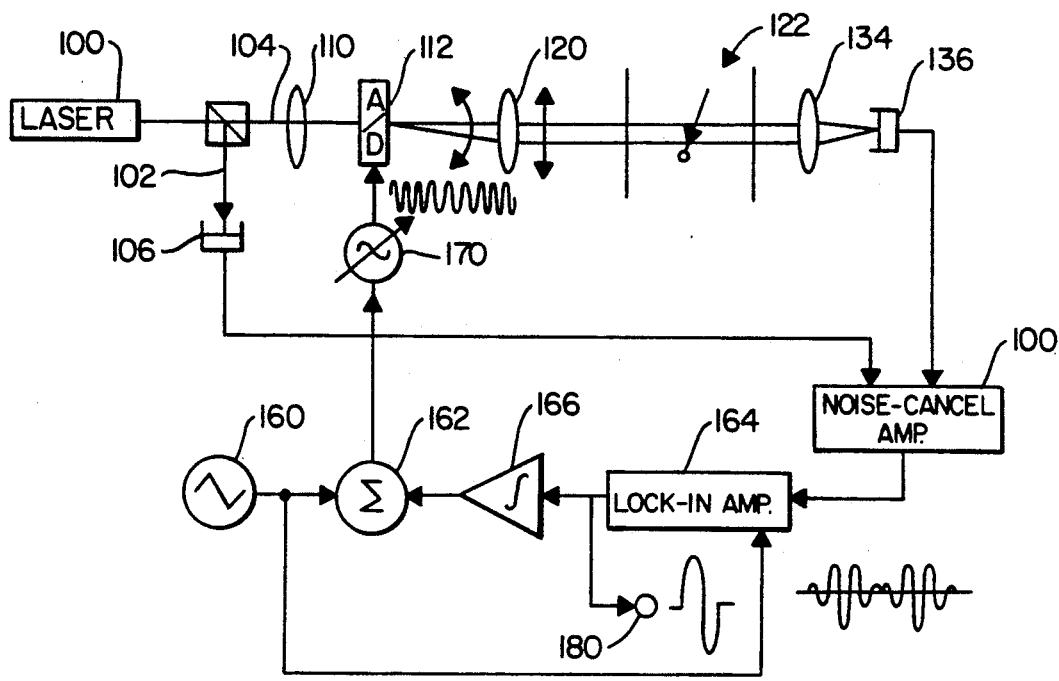
FIG. 8 is a schematic of a feedback network which enables artifacts to be removed from the system's signals.

One problem that can arise with the embodiment shown in FIG. 6 is that dithered beam 116 will produce a signal even with no particles present, if an anisotropic media resides in its beam path, such as a dirty flow cell window. Such false signals can reduce the sensitivity of the instrument. An embodiment which enables such background noise to be eliminated is shown in FIG. 8. In the embodiment of FIG. 8, it is preferred that the dither be oriented perpendicular to the flow to maximize the inspection volume. The portions of the system of FIG. 8 that are identical to those in FIG. 6 are similarly numbered.

Dither oscillator 160 provides either a symmetrical AC signal (e.g., a sine wave or a triangular wave) and applies it to a summing circuit 162. Another input to summing circuit 162 comes from lock-in amplifier 164 and integrator 166. The output of dither oscillator 160 is also applied to lock-in amplifier 164 as a reference. The output from summing circuit 162 is a DC level on which the dither voltage rides, and is applied to a voltage controlled oscillator 170 whose output is, in turn, applied as a controlling signal to acousto-optic deflector 112. As in the system of FIG. 6, acousto-optic deflector 112 causes the laser beam to move back and forth across a particle flow path at the dither frequency. It will be recalled, with respect to FIG. 6, that a particle present in inspection cell 122 will cause noise cancelling amplifier 108 to produce an oscillatory signal at the dither frequency.

For a small particle of extinction cross section $\delta t$ at a position (x,y), with a circular Gaussian laser beam of $1/e^2$ diameter, dithered sinusoidally a distance $2b$ peak to peak in the x direction, at angular frequency w, the extinction photocurrent is $$I_X = \frac{2I_0\sigma T}{\pi a^2} \exp\left( \frac{-2y^2 - 2(x - b\cos(\omega t))^2}{a^2} \right),$$

where $I_0$ is the total DC photocurrent. The fundamental component of this is $$I_{XF} = \frac{I_0\sigma T}{\sqrt{2\pi ab}} \exp\left(\frac{8x^2}{a^2} - \frac{\pi^2 a^2}{8b^2}\right) Im\left\{ e^{\frac{i\pi x}{b}} \left[ \begin{array}{l} crf\left(\frac{\sqrt{2}(b-2x)}{a} - \frac{i\pi a}{\sqrt{8}\,b}\right) + \\ crf\left(\frac{\sqrt{2}(b+2x)}{a} + \frac{i\pi a}{\sqrt{8}\,b}\right) \end{array} \right] \right\} \cos(\omega t)$$

Figure 9:
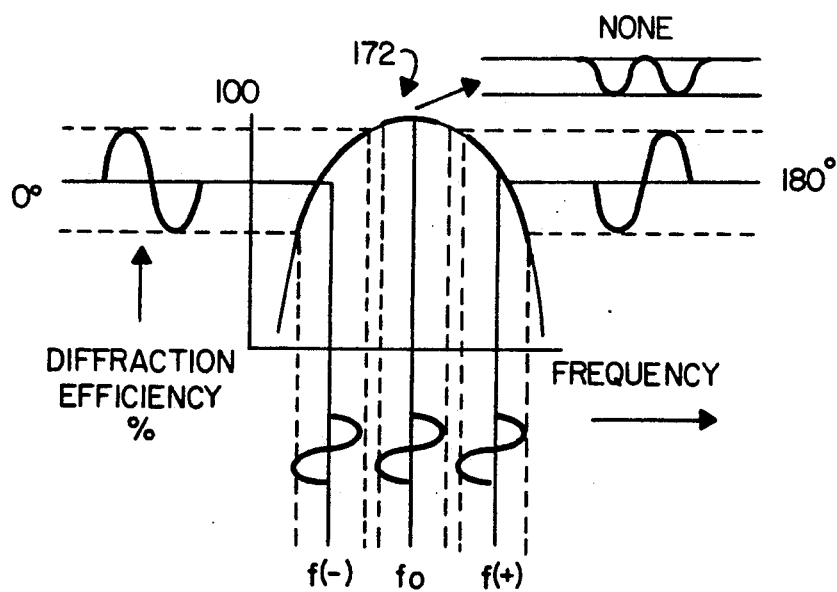
FIG. 9 is the response curve of an acousto-optic cell and a showing of how that response curve is used in providing correction signals in the system of FIG. 8.

The operation of the feedback control circuit for voltage control oscillator 170 is dependent upon the fact that the diffraction efficiency of acousto-optic cell 112 varies with frequency, being highest near the middle of its frequency band and decreasing smoothly as its band edges are approached. This response characteristic is shown in FIG. 9 at 172. It can there be seen that the modulation of acousto-optic cell 112 at a frequency above its center frequency (f+) results in one phase of optical modulation, while modulation at a frequency lower than its center of frequency (f−) results in an opposite phase modulation of the optical beam. This feature enables the feedback circuit to eliminate a persistent oscillating signal created by dirt or other artifact In addition, to prevent the feedback from affecting signals produced by particles in flow cell 122, the response time of the network is made long so that particle-generated oscillations are short relative to the response time of the feedback network and are passed to processor 142 before they can be acted upon and cancelled by the feedback.

Referring back to FIG. 8, and assuming that an artifact in the optical path creates a continuing oscillatory signal at the dither frequency, the output of noise cancelling amplifier 108 is fed to lock-in amplifier 164. Amplifier 164 is essentially a phase-sensitive detector. The dither signal from dither oscillator 160 is applied as another input to lock-in amplifier 164. The product of the dither oscillator signal and the input from noise cancelling amplifier 108 is applied as an input to integrator 166 which has a long time constant. The output from integrator 166 is a DC level that is proportional to the amplitude of the in-phase fundamental component of the output of noise cancelling amplifier 108. That DC level is fed through summing circuit 162 to voltage controlled oscillator 170 whose frequency is altered accordingly. As a result, the frequency applied to acousto-optic cell 112 is changed and causes its diffraction efficiency to alter in accordance with characteristics shown in FIG. 9.

If the applied frequency increases, the diffraction efficiency alters in accordance with the characteristic curve 172. The output of amplifier 108 then exhibits a 180° phase with respect to the dither voltage. On the other hand, if the applied frequency decreases from the center frequency, the diffraction efficiency decreases and the output of amplifier 108 is in phase with the dither voltage. The phase shift is always 0 degrees or 180 degrees.

If the output from noise cancelling amplifier 108 is in phase with the dither voltage (below center frequency $f_0$), lock in amplifier 164 produces a positive dc output that is proportional to A Cos 0, where A is the amplitude of the signal and 0 is the phase angle difference between the input signals. The positive dc potential is fed back via summing circuit 162 to voltage controlled oscillator 170, causing its frequency to increase. When the frequency exceeds center frequency $f_0$, the phase angle switches to 180° and the feedback causes lock in amplifier 164 to produce a negative dc output potential. That potential is fed back to voltage controlled oscillator 170 and causes a decrease in its frequency Thus, if the artifact gives a negative to positive (0 degree) fundamental component, the integrator's output will ramp up until the lock-in's output is zero (i.e. the artifact's contribution is nulled), and similarly for a 180 degree artifact signal. The action of the feedback loop ensures that the slowly-varying background signal at the fundamental is eliminated.

The system is thus immunized to slow changes in its optical properties. Any signal induced in the system by a particle in a flow cell occurs sufficiently rapidly that the slow feedback response is incapable of responding to it. As a result, an output signal is produced at terminal 180 that is indicative of only a particle (derived from the dithered beam as shown in FIG. 6). Output terminal 180 is connected to analog to digital convertor 140 and processor 142 as shown in FIG. 6.

The above described systems are particularly adapted to the characterization of particles with known or determinable flow directions. If particles are not moving, or are not moving in a known or steady direction, a "flow" dimension must be added to the beam motion since it is absent from the particle motion Additionally, the beam or beams must be dithered fast enough that the relative position of the particle with respect to the beams is known or determinable.

Figure 10:
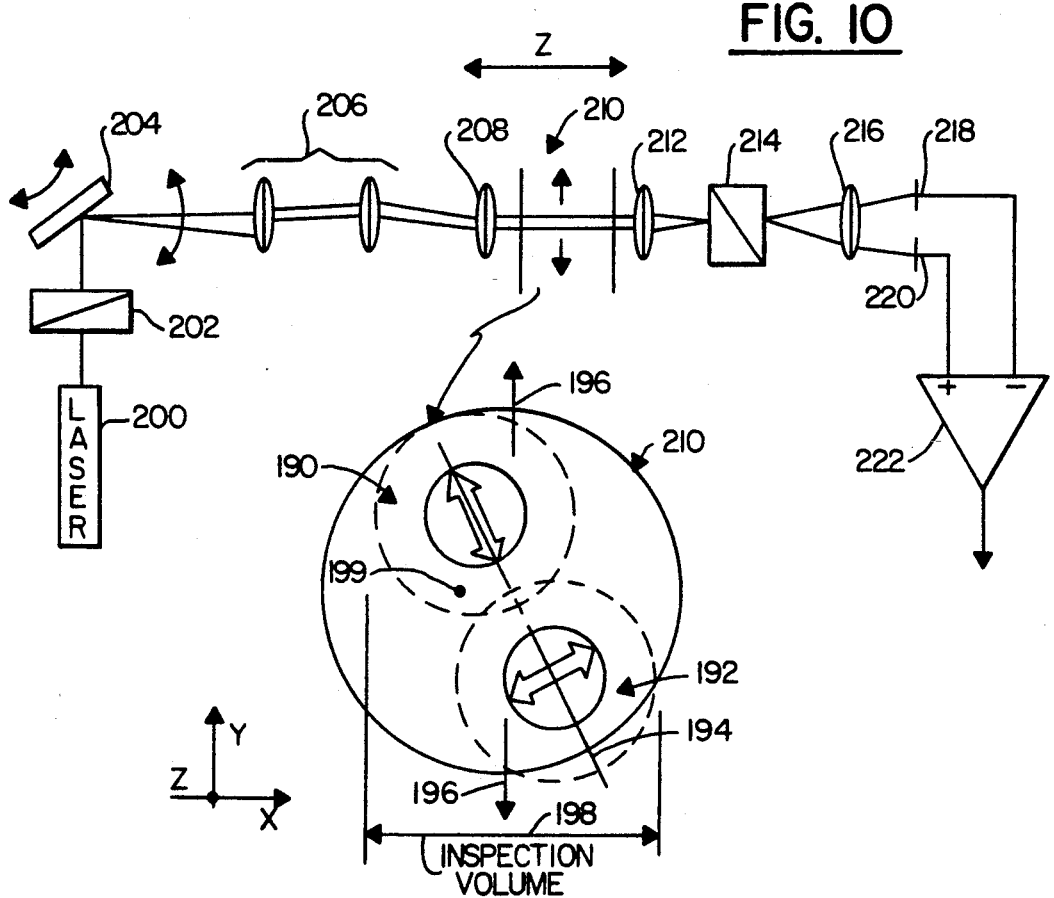
FIG. 10 is another embodiment of the invention showing an optical system which employs a pair of dithered beams to determine particle trajectory, when the direction of the trajectory is unknown.
Figure 11:
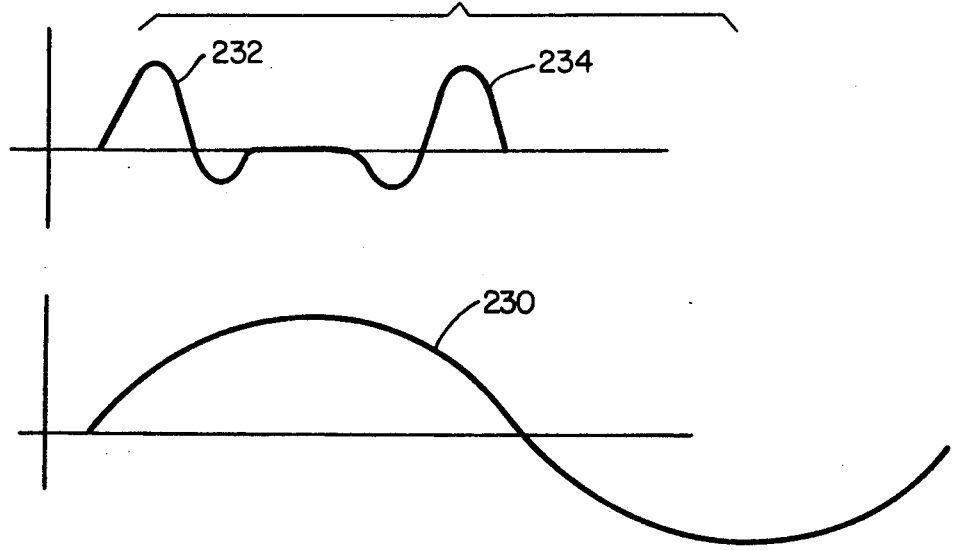
FIG. 11 shows two waveforms helpful in understanding the operation of FIG. 10.

Referring to FIGS. 10 and 11, a two beam system is shown which may be employed for non-flow systems or wherein a flow direction (if any) is unknown. As will be apparent from the following description, a pair of beams are dithered along a direction that is skewed to an imaginary line connecting the optical axes of the beams. Thus, as shown in FIG. 10 at 210 (an expanded plan view of a flow cell), orthogonally polarized beams 190 and 192 have their optical axes intersected by an imaginary line 194. The beams are controlled so that their scan is along the y direction indicated by arrows 196. That scan action creates an inspection volume as indicated by line 198. A particle 199 within inspection cell 210 will intersect beams 190 and 192 as they reciprocally move along direction 196.

If (see FIG. 11) the dither frequency is as shown at curve 230, particle 199 will cause the generation of waveforms 232 and 234, as beams 190 and 192 intersect particle 199. The opposing phases shown by waveforms 232 and 234 occur as a result of beams 190 and 192 moving in the upward direction during waveform 232, while they move in the downward direction to produce waveform 234.

The above-described beam motion and signals are produced by the system of FIG. 10 in the following manner. Laser 200 produces a beam polarization that is diagonal to the axes of Nomarski wedge 202. The output from Nomarski wedge 202 exhibits two divergent polarizations directed at a galvanometer controlled mirror 204. Mirror 204 angularly dithers the two polarized spots at an angle from the imaginary line (194) connecting the spots. A pair of relay lenses 206 then pass the dithering beams to a focus lens 208 where the beams are focussed into inspection cell 210. From there, the beams are passed through a collection lens 212, pass through Wollaston prism 214 (with axes aligned to those of the Nomarski prism), through an additional lens 216 where the orthogonally polarized beams are directed at photodetectors 218 and 220 respectively. From there, they are fed to a differential amplifier 222 whose output is shown by waveforms 232 and 234 in FIG. 11.

The system shown in FIG. 10 works on the extinction principal and waveforms 232 and 234 are generated as described previously with respect to the system of FIG. 1. The output from differential amplifier 222 is fed to a processor (not shown) for conversion to digital signals and then for analysis as aforedescribed.

A particle traversing inspection cell 210 will produce a bipolar signal burst, where the burst lasts as long as the particle remains in the region. The individual signals, as above-indicated, are asymmetric bipolar signatures that are identical to those described previously with respect to FIG. 1. Analysis of the individual signatures in the burst, using the same mathematics as described for FIG. 1 enables the path of the particle through the region to be obtained. If incomplete signals are produced from particles not within the dither region, they are to be ignored and can be identified by lack of two complete bipolar signals.

Figure 12:
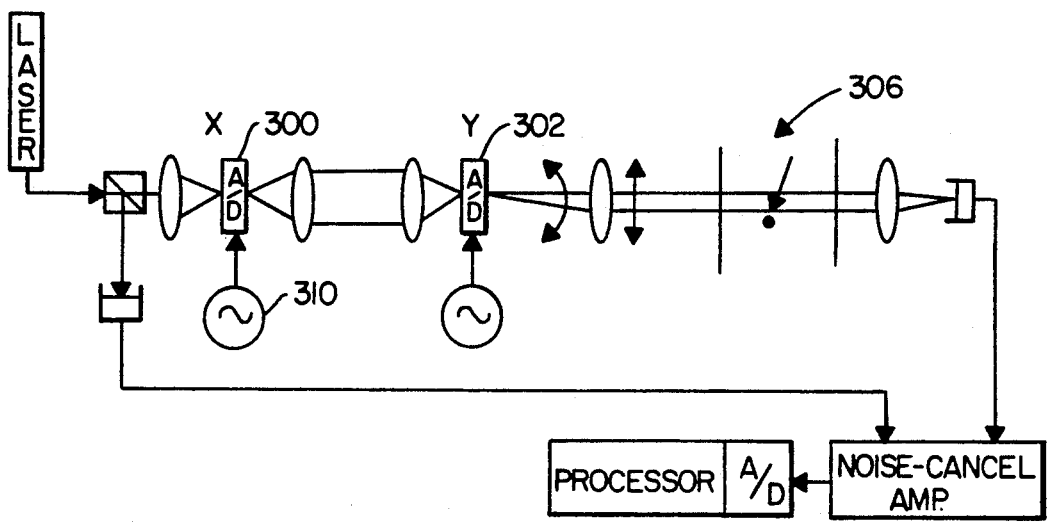
FIG. 12 is a schematic of another embodiment of the invention wherein a single beam is dithered in a pair of orthogonal directions.
Figure 13:
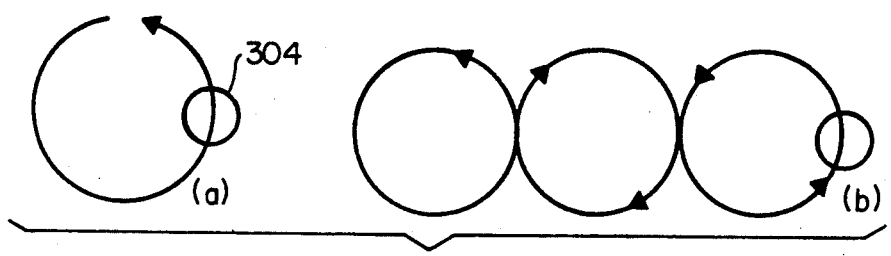
FIG. 13($a$) and 13($b$) show two dither configurations that are employable with the embodiment of FIG. 12.
Figure 14:
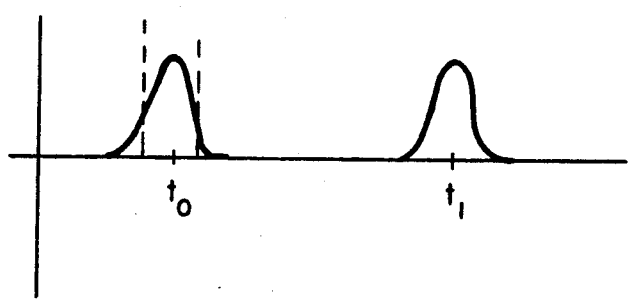
FIG. 14 shows a pair of waveforms which are obtained from the system of FIG. 12.

Turning now to FIGS. 12, 13 and 14, another embodiment of the invention is shown for non-flowing (or unknown flow-direction) particles wherein a single beam is multiply dithered. In this system, a pair of beam dither means are placed such that their dither directions are orthogonal. By dithering a beam rapidly in two orthogonal directions, information concerning a particle's position can be obtained.

In the system shown in FIG. 12, a pair of acousto-optic modulators 300 and 302 are oriented so that one modulator dithers a single beam in the X direction while the other modulator dithers the X-dithered beam in the Y direction. As a result (see FIG. 13), beam 304 experiences a circular path within inspection cell 306. A particle traversing the dither path of beam 304 will produce a signal maximum when it crosses the dither pattern (such as shown in FIG. 14) at time t0. Any particle which moves across the dithered region will produce two signal maxima (e.g., at t0 and t1). The FWHM of those signals will determine the out-of-focus distance, as described above, while the timing of the signal peaks with respect to the dither signals will show the entry and exit points along the dither pattern.

Particles which enter the pattern but do not leave, or approach it closely but do not enter, will produce only one peak and therefore can be distinguished and ignored. Additional information can be obtained with respect to a particle's position within the dither pattern if a more complex dither pattern is shown such as that used in FIG. 13(b). The illustrated dither pattern may be obtained by using x and y dither frequencies which are different multiples of a fundamental frequency (i.e. to create a Lissajous pattern).

DERIVATIONS

Part 1. Description of the optical system

This derivation assumes that a differential interference signal has been produced from a particle passing through two gaussian optical beams. The parameters for those beams are as follows:

| | |
|---|---|
| spot: = 10 | (spot size ($1/e^2$ intensity) in microns) |

$:=$ "is defined to be"

The spot size (or diameter) is the number of microns between two points on diametric opposite sides of the beam in the focal plane where the intensity at those points is 13.53% of the peak intensity at the center of the beam. It is assumed that both beams have the same spot size.

$$w_0 := \frac{spot}{2} \quad \text{(beam waist in microns)}$$

The beam waist is half the spot size.

| | |
|---|---|
| spacing: = 15 | (spot center-to-center spacing in microns) |

The beams are parallel as they propagate through the volume to be inspected. The distance between their optical axes in microns is spacing.

$$\text{twist angle:} = 17 \frac{\pi}{180} \quad \text{angle (in radians) between the center-to-center line and the } y \text{ axis (i.e., the particle flow path)}$$

The central or optical axes of the two beams define a plane. It is assumed that the medium being inspected moves perpendicularly to either beam such that the angle between the flow direction and the plane formed by the two optical axes is the complement of the twist angle. For example, if twist is zero, a possible trajectory would be to pass sequentially through the center of both beams. As twist gets greater, a particle passing through the optical axis of one beam will miss the optical axis the second beam by a greater amount.

The z axis is parallel to the optical axis of either beam. The y axis is parallel to the direction of flow of the material being inspected The origin is taken to be in the plane of focus at the mid-point between the two beams.

| | |
|---|---|
| $\lambda: = 0.78$ | laser wavelength in microns |
| $n: = 1.33$ | index of refraction of the liquid |

How fast the laser beams spread out as they leave focus will depend on their wavelength and the index of refraction of the medium being inspected.

$$z_0: \frac{w_0^2 \cdot n \cdot \pi}{\lambda} \quad \text{depth of focus, in microns. } z_0 = 133.92$$

The depth of focus is the distance on either side of the focal plane where the area of the spot has increased by a factor of two over the area at focus. This is also known as the Rayleigh range.

Part II. The measured parameters

In a typical case, a particle creates two sequential pulses from the detector measuring the phase difference between the two optical paths of the two beams. The two pulses occur as the particle passes through first one and then the other beam. Generally speaking, one peak will be positive going and the other negative; whether the first will be positive or not depends on the relative index of the particle and the sign conventions in the optics and electronics. It is assumed in this derivation that the first pulse is positive. The five measured parameters that are used in this analysis are:

1) Tdiff: time delay between the first peak and the second peak
2) T1: time during which the first peak was greater than 50% of its peak amplitude (FWHM)
3) T2: time during which the second peak was more than 50% of its minimum amplitude
4) Peak1: the maximum value of the first peak
5) Peak2: the absolute value of the minimum of the second peak

Part III. Velocity

There are two types of normalizations that should be performed. The first is because the above time delay values vary proportionally with the velocity. Therefore the velocity information is extracted (because it is useful in calculating the flow rate and the observed particle concentrations) and removed from the peak widths.

$$\text{Velocity:} = \frac{spacing}{Tdiff} \quad \text{measured flow velocity}$$

$$FWHM1: = \frac{T1 \; spacing}{Tdiff} \quad \text{FWHM of the first peak, in microns}$$

$$FWHM2: = \frac{T2 \; spacing}{Tdiff} \quad \text{FWHM of the second peak, in microns}$$

Second, the ratio of the smallest peak height (in absolute value) to the largest peak height (the asymmetry of the signal) is normalized to a number between 0 and 1 for all signals.

part IV. Distance from focal plane

When a particle goes through the optical axis of one of the two beams while in the plane of focus, the FWHM of the resulting peak is:

$$FWHM0: = (spot) \sqrt{\ln(2)} \quad FWHM0 = 8.326 \text{ microns}$$

Assume the measured the widths of two actual peaks in a given signal to be 10.4 and 11.2 microns (empirically measured). The following formula enables reconstruction of the distance z from the plane of focus that the particle travelled:

$$FWHM1: = 10.4 \quad FWHM2: = 11.2$$

$$z: = z_0 \cdot \sqrt{\left[\frac{FWHM1 + FWHM2}{2 \, FWHM0}\right]^2 - 1}$$

$$z = 110.657 \text{ microns}$$

In this case, the trajectory of the particle was approximately 111 microns from the plane of focus. That result is used to determine the spot size for the subsequent off axis calculation.

$$w := w_0 \cdot \left[\frac{FWHM1 + FWHM2}{2FWHM0}\right] \text{ beam waist away from focus}$$

$$w = 6.486$$

Part V. Distance from central axis

There is no analytical solution that will generate the distance of closest approach to the central axis (the z axis in the geometry described above) from the measurable parameters. Instead the asymmetries are precalculated for different distances of closest approach, and then compared and interpolated to derive the actual distance by comparing the observed asymmetry to the table of calculated asymmetries. Begin by calculating the asymmetries that result when particles with different initial x positions (the distance of closest approach to the z axis) pass through the two beams.

number of distances: = 60;
$i := 0 \ldots$ number of distances
$i$ is an index variable and can be 0, 1, 2, ... to 60.

$$x_i := \frac{(\text{spot} + (\text{spacing})\sin(\text{twist})) \cdot i}{b = \text{number of distances}} \text{ distances of closest approach, in microns}$$

$$xs := \frac{\text{spacing}}{2}(\sin(\text{twist}));$$

$$ys := \frac{\text{spacing}}{2}(\cos(\text{twist}))$$

The variables xs and ys are functions used to simplify following expressions. The optical axes of the two beams intersect the focal plane at (xs,ys) and (−xs,−ys).

The signal generated by the particle in the plane of focus will be proportional to $$\text{signal}(x,y) := \exp\left[\frac{-[(x-xs)^2 + (y-ys)^2]}{w^2}\right] - \exp\left[\frac{[-(x-xs)^2 + (y-ys)^2]}{w^2}\right]$$

The signal is the difference of two gaussians representing the amplitudes of the two different beams.

To find the values of the peaks of the signal for a given off-axis distance x, the derivative is taken of the signal with respect to y, set equal to 0 and solved for the position y. Since there are two peaks, there are two possible places where the derivative will be zero. Use the initial value of spacing for $\tilde{y}$ to get the first value.

$$y := \frac{\text{spacing}}{2} \text{ initial guess for } y \text{ value}$$

$$a_i := \text{root}\left[\frac{d}{dy} \overline{\text{signal }[x_i,y]}, y\right] \begin{array}{l}y \text{ position where}\\ \text{plus peak is reached}\end{array}$$

Now do the same thing for the negative peak.

$$y := \frac{-\text{spacing}}{2} \text{ initial guess for } y \text{ value}$$

$$b_i := \text{root}\frac{d}{dy} \overline{\text{signal } x_i,y}, y \begin{array}{l}y \text{ position where}\\ \text{minus peak is reached}\end{array}$$

The ratio of the positive peak to the negative peak gives the asymmetry at the distance of closest approach.

$$\text{asymmetry}_i := \frac{-\text{signal }[x_i,b_i]}{\text{signal }[x_i,a_i]}$$

Part VI. Size correction

The purpose of getting the particle's trajectory is to remove the error in the signal size that occurred because the particle did not go through the exact center of the optical beams. This is accomplished by computing a correction factor. The correction factor is a number that multiplies the height of the larger of the two peaks from the particle signal so as to produce a peak height that would occur if the particle had gone precisely through the z axis (thereby producing a symmetric signal, with the plus and minus peaks being of equal size).

$$\text{correction}_i := \frac{-\text{signal }[x_0,a_0]}{\text{signal }[x_i,a_i]}$$

Part VII. Volume correction

Next is computed the maximum off-axis distance for which a particle of a given size can be seen. This sets the effective inspection volume for particles of that size.

For example, polystyrene spheres (often used for calibration) in water produce phase signals that are proportional to the cube of the particle diameters. A particle with diameter size1 is found to be detectable a distance x1 from the y-z plane. A different particle with diameter size2 would then be detectable a distance x2 from the y-z plane, where x2 satisfies the relationship Minimum detectable peak := (size1$^3$) (signal (x1,b1))
= (size2$^3$)(signal(x2,b2))

b1 and b2 are the y positions to achieve the smaller of the two peaks for each particle, respectively. As the size gets bigger, the distance from the y-z plane where the particle can be detected gets bigger.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. An apparatus for determining a particle's position in a flow path having a determinable direction comprising:
    means for transmitting to a flow path, first and second substantially parallel optical beams, said beams being initially mutually coherent but of different polarizations, said second beam offset from said first beam along an axis that intersects said determinable direction at an acute twist angle, a particle that passes through a beam inducing a phase shift in said beam that decreases as the distance increases of the particle from said beam's optical axis;

recombining means positioned in a path which said beams take after departing from said flow path, for combining said beams, a phase shift in a said beam causing said combined beam to manifest an elliptical polarization exhibiting first and second polarization axes;

detector means for sensing an intensity of one of said elliptical polarization axes to provide a phase shift signal; and processing means for accumulating phase shift signals resulting from a particle's travel in said flow path past said first and second beams, and subtracting a phase shift signal derived from said first beam from a phase shift signal derived from said second beam to determine an asymmetry value indicative of said particle's position in said flow path.

2. The apparatus as recited in claim 1 wherein said beams exhibit substantially the same diameter and are offset from each other in both x and y dimensional directions, the beams being separated along the x direction by a distance which is in the range of 0.05 to 0.35 of a beam diameter.

3. The apparatus as recited in claim 1 wherein a said phase shift signal exhibits bipolar succeeding peaks, one said peak exhibiting a lower absolute amplitude than a second peak if said particle is offset from a central flow path.

4. The apparatus as recited in claim 1 wherein said processing means includes a stored table of asymmetry values for different distances of a particle from said central flow path, said processing means employing said determined asymmetry value and asymmetry values stored in said respect to said central flow path.

5. The apparatus as recited in claim 1 wherein said detector means comprises:

means for prod two beams from said combined beam, a first said beam exhibiting said first polarization axis and a second said beam exhibiting said second polarization axis;

sensor means for detecting intensities of said first and second beams; and differential means responsive to said sensor means for eliminating common mode noise from said detected intensities.

6. An apparatus for determining a particle's position in a flow path comprising:

means for transmitting to a focal plane in said flow path, first and second substantially parallel optical beams, said beams being initially mutually coherent but of different polarizations, said beams displaced from each other along said flow path, a particle in said flow path that passes through a beam inducing a phase shift and change in extinction of said beam;

recombining means positioned in a path which said beams take after departing from said flow path for combining said beams, a phase shift in a said beam causing said combined beam to manifest an elliptical polarization exhibiting first and second polarization axes;

detector means for sensing an intensity of at least one of said polarization axes to provide a phase shift signal;

processing means for accumulating phase shift signals resulting from a particle's travel in said flow path, to derive a phase shift waveform therefrom, and for measuring a width characteristic of said phase shift waveform and deriving from said width characteristic an indication of the position of said particle relative to said focal plane.

7. The apparatus as recited in claim 6 wherein said phase shift signal exhibits succeeding bipolar peaks, said processing means employing measured width characteristics of said succeeding peaks, and determined width characteristics of a phase shift signal that would be produced if said particle intersected said beams at said focal plane, to derive a correction factor, said processing means further combining said derived correction factor with said derived phase shift waveform to produce characteristics of a waveform that would have been produced had said particle passed through said focal plane.

8. The apparatus as recited in claim 6 wherein said detector means comprises:

means for producing two beams from said combined beam, a first said beam exhibiting said first polarization axis and a second said beam exhibiting said second polarization axis;

sensor means for detecting intensities of said first and second beams; and differential means responsive to said sensor means for eliminating common mode noise from said detected intensities.

9. An apparatus for determining a particle's position in a flow path having a determinable direction, comprising:

means for transmitting to a flow path at least an optical beam;

dither means for oscillating said optical beam across said flow path at a rate that is high in relation to a rate of travel of a particle in said flow path, a particle in said flow path causing a change in extinction in said optical beam when said beam intercepts said particle;

sensor means for providing output signals indicative of the extinction of said beam and including a noise cancelling amplifier provided with an input from said transmitting means, whereby said amplifier provides a minimal signal output at times other than when a particle in said flowpath intersects said beam; and processor means for sampling said output signals and deriving an extinction signal profile resulting from a said particle's travel in said flow path.

10. The apparatus as recited in claim 9 wherein said dither means moves said optical beam at an acute angle with respect to said determinable direction.

11. The apparatus as recited in claim 10 wherein said acute angle lies in the range of 15° to 20°.

12. The apparatus as recited in claim 11, wherein said optical beam, at extremities of its cyclic dither travel, defines an inspection volume within which particle positions can be determined 13. The apparatus as recited in claim 12 wherein said processor means derives said extinction signal profile from samples of said sensor output taken at each extremity of cyclic dither travel of said beam.

14. The apparatus as recited in claim 13 wherein said processor means employs said derived extinction signal profile to determine an asymmetry value indicative of said particle's position in a flow path.

15. The apparatus as recited in claim 13 wherein said processor means measures a width characteristic of said derived extinction signal profile and derives therefrom an indication of the position of said particle relative to a focal plane in said flow path.

16. The apparatus as recited in claim 9 wherein said dither means exhibits a diffraction efficiency characteristic which decreases on either side of a center frequency, a non-particulate artifact in the path of said optical beam causing a center frequency component in said output signal, the combination further comprising:
- a variable frequency oscillator for energizing said dither means;
- a feedback circuit responsive to a dither frequency component in said output signals for providing a delayed acting feedback signal to said variable frequency oscillator to vary its frequency about said center frequency, whereby said diffraction efficiency is altered to substantially remove said center frequency component from said output signals.

17. The apparatus as recited in claim 16 wherein said feedback circuit includes integrating means to provide said delayed-acting feedback signal, whereby said feedback signal is ineffective to alter an output signal from said sensor means that is caused by a particle in said flow path.

18. The apparatus as recited in claim 17 wherein said feedback circuit further includes:
- a dither oscillator;
- a comparison circuit for comparing the phase of said sensor output signals with the phase of said dither oscillator and for providing a correction signal to said integrating means in response to said phase comparison; and
- summer means for combining outputs from said dither oscillator and integrating means and applying said combined outputs to vary the frequency of said variable frequency oscillator.

19. An apparatus for determining a particle's position in a flow cell, said particle's flow direction path being indeterminate, comprising:
- means for transmitting to said flow cell, first and second substantially parallel optical beams, said beams being initially mutually coherent but of different polarizations, said beams displaced from each other along an axis, a particle in said cell that intercepts a beam inducing a change in intensity of said beam;
- dither means for cyclically moving said optical beams across said flow cell in a direction at an angle with respect to said axis;
- a pair of detector means, one said detector means responsive to said first beam's intensity to produce a first output, and another said detector means responsive to said second beam's intensity to produce a second output;
- means for combining said first and second outputs to provide a composite signal; and
- processing means for accumulating composite signals resulting from a particle's interception of said dithered beams to derive a waveform therefrom, and for determining said particle's position from said waveform.

20. The apparatus as recited in claim 19 wherein said dither means simultaneously moves both said optical beams reciprocally along said direction so as to cause at least one said beam to intercept a said particle.

21. The apparatus as recited in claim 20 wherein said beams are displaced along said axis at a distance which enables both said beams to overlap and create a continuous inspection volume as they are moved along said direction.

22. An apparatus for determining a particle's position in a flow cell, said particle's flow direction being indeterminate, comprising:
- means for transmitting to said flow cell, a coherent optical beam, a particle in said cell that intercepts said beam inducing a change in extinction of said beam;
- dither means for cyclically moving said optical beam in said flow cell in a pattern that closes upon itself and encompasses an inspection region;
- detector means responsive to said beam's extinction to produce first output signals; and
- processing means for accumulating said first output signals resulting from a particle's interception of said dithered beam to derive a waveform therefrom and for determining said particle's position from said waveform.

23. The apparatus as recited in claim 22 wherein said dither means moves said optical beam in a closed, substantially circular pattern.

24. The apparatus as recited in claim 23 wherein said dither means moves said optical beam so as to trace a plurality of closed patterns.

25. An apparatus for determining a particle's position in a flow path, comprising:
- means for transmitting to said flow path, first and second optical beams, said beams being initially mutually coherent but of different polarizations, said second beam offset from said first beam along an axis that intersects said flow path at an acute twist angle, a particle that intersects a beam inducing a change in a said beam;
- recombining means positioned in a path which said beams take after departing from said flow path, for combining said beams, a change in a said beam causing said combined beam to manifest an elliptical polarization exhibiting first and second polarization axes;
- detector means for sensing an intensity of one of said polarization axes to provide a signal; and
- processing means for accumulating said signals resulting from a particle's travel in said flow path past said beams, and for determining an asymmetry value of said signal indicative of said particle s position in said flow path and a further value indicative of said particle's position relative to a focal plane in said flow path, said processor further determining from said values and from stored, allowed off-axis and out-of-focus distances, whether the particle resides in an allowed inspection volume.

* * * * *

UNITED STATES PATENT AND TRADEMARK OFFICE
CERTIFICATE OF CORRECTION

PATENT NO. : 5,133,602
DATED : July 28, 1992
INVENTOR(S) : Batchelder, et. al.

It is certified that error appears in the above-indentified patent and that said Letters Patent is hereby corrected as shown below:

Col. 17, line 41, after "said" (1st occurrence) insert --table to determine a said particle's position with --.

Col. 17, line 44, change "prod" to -- producing --.

Col. 20, line 54, delete "said".

Col. 20, line 57, "particles s" should read -- particle's --.

Signed and Sealed this

Twenty-fourth Day of August, 1993

Attest:

BRUCE LEHMAN

*Attesting Officer*      *Commissioner of Patents and Trademarks*